United States Patent [19]
Bartolone et al.

[11] Patent Number: 6,153,177
[45] Date of Patent: Nov. 28, 2000

[54] SKIN LIGHTENING COMPOSITION

[75] Inventors: John Brian Bartolone, Edgewater, N.J.; Govindarajan Raman, Bangalore, India; Pushker Sona; Ramesh Surianarayanan, both of Mumbai, India; Sushama Shripad Wagh, Bangalore, India

[73] Assignee: Chesebrough-Ponds's USA, Co., division of Conopco, Inc., Greenwich, Conn.

[21] Appl. No.: 09/211,831

[22] Filed: Dec. 15, 1998

[30] Foreign Application Priority Data

Dec. 15, 1997 [IN] India ............................................. 721/97
Jan. 26, 1998 [GB] United Kingdom ................... 9801597

[51] Int. Cl.⁷ .......................... A61K 7/135; A61K 31/74
[52] U.S. Cl. .............................................. 424/62; 424/401
[58] Field of Search ................................. 424/78.03, 401, 424/62; 514/844

[56] References Cited

U.S. PATENT DOCUMENTS

| | | | |
|---|---|---|---|
| 5,262,153 | 11/1993 | Mishima et al. | 424/62 |
| 5,658,580 | 8/1997 | Mausner | 424/401 |
| 5,902,591 | 5/1999 | Herstein | 424/401 |
| 5,997,890 | 12/1999 | Sine | 424/401 |

FOREIGN PATENT DOCUMENTS

| | | |
|---|---|---|
| 345 081 | 12/1989 | European Pat. Off. . |
| 423 929 | 4/1991 | European Pat. Off. . |
| 2 287 405 | 9/1995 | United Kingdom . |
| 95/05153 | 2/1995 | WIPO . |
| 96/37179 | 11/1996 | WIPO . |
| 97/47280 | 12/1997 | WIPO . |
| 98/27193 | 6/1998 | WIPO . |

OTHER PUBLICATIONS

G.B. Search Reported in the application of GB 9801597.7.
International Search Report in the application of PCT/EP 98/081470.

*Primary Examiner*—Thurman K. Page
*Assistant Examiner*—S. Howard
*Attorney, Agent, or Firm*—Radha Masilamani

[57] ABSTRACT

A cosmetic skin lightening composition for topical application to human skin comprising (A) 5–25% by weight fatty acids, (B) 0.1–10% by weight fatty acid soap and (C) 0.05–10% by weight alkali or alkaline earth metal salt of α-hydroxy carboxylic acid and/or α-acyloxy carboxylic acid.

8 Claims, No Drawings

SKIN LIGHTENING COMPOSITION

The present invention relates to a cosmetic composition for lightening the skin. The invention also relates to a method of topically applying to the skin a skin lightening composition according to the invention.

Melanin is the black pigment of hair and skin and is synthesized from the amino acid tyrosine by melanosomes. Melamosomes are organelles found in melanocytes, a cell type present at the dermis-epidermis junction. Tyrosine is acted upon by an enzyme, tyrosinase, which is the key step in melanogenesis. There have been several reports wherein inhibitors of tyrosinase such as hydroquinone and its derivatives, catechols, mercaptoamines, alpha hydroxy acids and others have been used in cosmetic compositions to regulate skin pigmentation. However, only some of these are reversible and show no undesirable side effects.

In the melanosomes melanin is synthesised from monomers and is transferred to the neighbouring keratinocytes. The keratinocytes divide and differentiate and thus transport the melanosome to the surface of the skin. The intensity of the skin colour is directly related to the number, the size, the melanin content, the rate of formation and migration transfer of melanosomes to the keratinocytes.

Conventional skin lightening compositions are based on sunscreens or skin lightening agents. The latter are believed to control dispersion of melanosomes or inhibit tyrosinase. Sunscreens alone cannot lighten the skin beyond the natural skin colour and their only action is to reduce the ingress of ambient ultraviolet radiation into the skin.

Thus, they exert their effect only during the day, some of the compounds used as skin lightening agents are also known to have undesirable side effects.

Use of $\alpha$-hydroxy acids in cosmetic compounds for imparting various skin benefits such as improving the texture of the skin, increasing smoothness, firmness, moisture content is reported in U.S. Pat. No. 5,658,580. U.S. Pat. No. 5,262,153 discloses lactic acid and its derivatives as useful skin whitening agents which act by suppressing melanogenesis by inhibiting formation of tyrosinase.

Cosmetic compositions to deliver different benefit agents are prepared using different emulsifying systems and vehicles. Vanishing cream base which generally comprises fatty acids and alkali metal soaps is one of the preferred forms of such a cosmetically acceptable vehicle as this gives a desirable matt feel to the skin. Unfortunately, however, lactic acid, which is known as a skin lightening agent, cannot be used in vanishing creams since lactic acid substantially lowers the pH and thereby destabilises the base.

It has now been found that alkali metal and alkaline earth metal salts of $\alpha$-hydroxy and $\alpha$-acyloxyl-carboxylic acids also have a skin lightening effect and, advantageously, that these salts can effectively be delivered to the skin in a vanishing cream base.

It is therefore an object of the present invention to provide a cosmetic composition to deliver lactic acid derivatives to the skin through a vanishing cream base for obtaining skin lightening benefit.

Accordingly, the present invention relates to a cosmetic skin lightening composition for topical application to human skin comprising:

A. 5–25% by weight C12–C20 fatty acids;
B. 0.1–10% by weight fatty acid soap;
C. 0.05–10% by weight of alkali or alkaline earth metal salt of $\alpha$-acyloxy carboxylic acid;

The skin lightening effected by the composition of the invention is reversible and without any side effects. The composition according to the invention is active during both day and night.

Preferably, the alkali or alkaline earth metal salt is of lactic acid and/or acyloxyl lactylate. Most preferably the salt is of stearoyl lactylate.

According to more preferred aspect of the invention the cosmetic composition comprises at least 0.05% by weight of an alkali metal salt of stearoyl lactylate.

Particularly suitable salt of $\alpha$-hydroxy carboxylic acid or the $\alpha$-acyloxyl carboxylic acid is the sodium salt.

The composition preferably comprises 10–20% by weight of C12–C20 fatty acids.

The composition most preferably comprises C14–18 fatty acids. The fatty acid soap preferably comprises 1–5% by weight of the composition. The fatty acids and fatty acid derivatives are preferably saturated.

According to a further aspect of the present invention there is provided a cosmetic method for lightening human skin by topically applying to the skin a skin lightening composition according to the invention.

The composition may also comprise an additional skin lightening agent which may be chosen from any known such agent for example: niacin, niacinamide, placenta extract, hydroquinone and derivatives (e.g. arbutin), kojic acid, dicarboxylic acids (azelaic acid, sebacic acid), represented by the formula HOOC—(CxHy)—COOH where x ranges from 4 to 20 and y ranges from 6 to 40, ascorbic acid and derivatives thereof and ferulic acid. Further skin lightening agents may be retinol and derivatives, organic sunscreens such as 4-tertiary butyl-4'-methyoxy dibenzoylmethane, and/or 2-ethyl hexyl methoxyl cinnamate, inorganic sunscreens such as micronised titanium dioxide, zinc oxide or other UV A and UV B sunscreens and other known skin lightening compounds. The preferred skin lightening agents are niacin and niacinamide. The composition may comprise 0–10% by weight of the additional skin lightening agent.

The composition according to the invention may also comprise cosmetically compatible preservatives, thickeners, perfume, colour, skin benefit materials such as humectants, emollients and antiageing compounds.

The composition may also comprise small amounts of other cosmetically emulsifiers preferably not more than 10% by weight, more preferably less than 5%.

Examples of moisturisers and humectants include polyols, glycerol, cetyl alcohol, paraffin oils, lanolin and its derivatives, fatty acid esters, etc. Silicone compounds such as silicone oil, cyclomethicones, dimethicones, dimethiconols may also be included.

All the percentages referred to herein and in the appended claims are by weight of the composition unless otherwise indicated.

The invention will now be illustrated by way of Examples. The Examples are for illustration only and do not in any way restrict the scope of the invention.

EXAMPLE

A. Composition of the Creams

The invention will now be illustrated by reference to the following examples of cosmetic creams presented in Table 1.

TABLE 1

| COMPOSITION % wt. | EXAMPLE 1 | EXAMPLE 2 | EXAMPLE 3 |
|---|---|---|---|
| Stearic acid | 15.0 | 15.0 | — |
| Cetosteryl alcohol | 0.6 | 0.6 | 10.0 |

TABLE 1-continued

| COMPOSITION % wt. | EXAMPLE 1 | EXAMPLE 2 | EXAMPLE 3 |
|---|---|---|---|
| Humectants | 1.0 | 1.0 | 1.0 |
| Emollients | 0.5 | 0.5 | 3.5 |
| Soap | 2.5 | 3.0 | — |
| Nonionic emulsifiers | — | — | 2.5 |
| Thickeners | 3.3 | | |
| Sunscreens | 1.65 | — | 1.65 |
| Methyl/propyl paraben/EDTA | 0.4 | 0.4 | 0.4 |
| Perfume | 0.2 | 0.2 | 0.2 |
| Actives | 8.0# | 5.0@ | 8.0* |
| Water | To 100% | To 100 | To 100% |
| pH | >5.0 | >5.0 | >5.0 |

5% lactate + 2% Sodium stearoyl lactylate + 1 Niacinamide
@Sodium stearoyl lactylate
*8% lactate The figures in the table represent percentages of the composition by weight.

B. Effect on Skin Lightening

A panel of 25 volunteers was maintained for each assessment after screening the forearms of the panelists for uniformity of colour. Measured dose of the cream (Example 1, 2 or 3) was applied to one of the forearms twice a day. Visual assessment was carried out for a period of 8 weeks. The level of skin lightening is presented in Table 2.

TABLE 2

| COMPOSITION OF THE CREAM | SKIN LIGHTENING EFFECT |
|---|---|
| Example 1 | −0.39 |
| Example 2 | −0.35 |
| Example 3 | −0.52 |

It is thus possible by way of the present invention to provide for a skin lightening composition which is reversible and without any side effects. The composition is active both during the day and night.

What is claimed is:

1. A cosmetic skin lightening composition for topical application to human skin comprising:

A. 5–25% by weight C12–C20 fatty acids

B. 0.1–10% by weight fatty acid soap

C. 0.05–10% by weight alkali or alkaline earth metal salt of α-acyloxy carboxylic acid.

2. A cosmetic skin lightening composition according to claim 1 wherein the alkali or alkaline earth metal salt is of acyloxy lactylate.

3. A cosmetic skin lightening composition according to claim 2 wherein the acyloxyl lactylate is steroyl lactylate.

4. A cosmetic skin lightening composition according to any preceding claim that comprises the sodium salt of α-acyloxy carboxylic acid.

5. A cosmetic skin lightening composition according to claim 1 that comprises 10–20% by weight of the C12–C20 fatty acids.

6. A cosmetic skin lightening composition according to claim 1 that comprises 1–5% by weight of the fatty acid soap.

7. A cosmetic skin lightening composition according to claim 1 that comprises an additional skin lightening agent.

8. Cosmetic method for lightening skin by topically applying to the skin a composition according to any preceding claim.

* * * * *